United States Patent [19]

Sanders et al.

[11] Patent Number: 4,620,004
[45] Date of Patent: Oct. 28, 1986

[54] POLYHETEROCYCLIC COMPOUNDS

[75] Inventors: Edward B. Sanders; Yoram Houminer, both of Richmond, Va.

[73] Assignee: Philip Morris Incorporated, New York, N.Y.

[21] Appl. No.: 220,196

[22] Filed: Dec. 23, 1980

Related U.S. Application Data

[62] Division of Ser. No. 45,716, Jun. 5, 1979, Pat. No. 4,318,418.

[51] Int. Cl.$^4$ ............................................ C07D 241/02
[52] U.S. Cl. .................... 544/357; 544/362; 544/405; 544/349; 546/255; 131/278; 252/522 A
[58] Field of Search ................... 252/522 A; 544/357, 544/349, 338, 336, 350, 362, 353, 405; 131/270, 277, 276, 275; 546/255

[56] References Cited

PUBLICATIONS

Chemical Abstract 92:128091x; "Photoaddition Reactions . . . "; Shim et al.; 1979.

Chemical Abstract 87:200487x; "Photochemical Reduction . . . "; Shim et al.; 1977.

Primary Examiner—V. Millin
Assistant Examiner—Gregory Beaurage

[57] ABSTRACT

This invention provides polyheterocyclic compound useful as a flavorant additive.

In one embodiment, this invention provides a polyheterocyclic flavorant additive for smoking compositions such as 1,2-bis(3,5,6-trimethyl-2-pyrazyl)ethane:

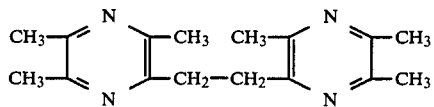

Under smoking conditions the above illustrated polyheterocyclic additive flavors the mainstream and sidestream smoke.

In another embodiment, this invention provides a polyheterocyclic such as 1-(3,5,6-trimethyl-2-pyrazyl)-2-(2-pyridyl)ethane.

10 Claims, No Drawings

POLYHETEROCYCLIC COMPOUNDS

This is a division of application Ser. No. 45,716 filed June 5, 1979, now U.S. Pat. No. 4,318,418.

BACKGROUND OF THE INVENTION

It has been established that alkylpyrazines are natural components of tobacco smoke, and that they most probably are important contributors to tobacco smoke flavor [A. Baggett et al, *J. Chromatog*, 97, 79 (1974)]. Further, it has been disclosed in the patent literature that addition of alkylpyrazines to tobacco results in an improvement in the flavor of smoking compositions as perceived by a test panel.

British 1,244,068 describes a method for influencing the smoke flavor of tobacco or a tobacco mixture which consists of treating the tobacco with a pyrazine derivative of the following chemical structure:

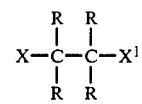

in which each R is independently a hydrogen atom, an aliphatic radical, an alicyclic radical or an aromatic hydrocarbon radical, such radicals having up to 9 carbon atoms, or R is a heterocyclic radical containing 4 to 9 carbon atoms.

U.S. Pat. No. 3,402,051 decribes a process for imparting a popcorn-like flavor and aroma to tobacco and foodstuffs by the incorporation of a 2-acetylpyrazine derivative therein.

Other patents which disclose the addition of various pyrazine compounds to tobacco and foodstuffs as a means of providing flavor or flavor enhancement include U.S. Pat. Nos. 3,684,809; 3,686,177; 3,705,158; 3,748,145; 3,754,934; 3,764,349; 3,767,426; 3,773,525; and 3,881,025.

Alkylpyridines have also been found to be useful tobacco additives. As an example, U.S. Pat. No. 3,625,224 describes the use of methylpyridines, ethylpyridines and various dialkylpyridines as tobacco additives. U.S. Pat. No. 3,381,691 discloses 2-methyl-5-isopropylpyridine as a tobacco additive.

It is characteristic of both pyrazine and pyridine derivatives employed as tobacco flavorants in the prior art, as illustrated by the above described technical literature, that the respective heterocyclic derivatives have the disadvantage of both high volatility and low odor threshold. Both of these properties significantly restrict the extent that these heterocyclic derivatives can be utilized as flavorants in tobacco compositions. A quantity of a pyrazine or pyridine derivative in a tobacco composition sufficient to have a noticeable effect in low delivery cigarettes causes a marked pack aroma.

Accordingly, it is a main object of this invention to provide [tobacco and non-tobacco smoking compositions which have incorporated therein] a polyheterocyclic compound useful as a flavorant additive for smoking compositions which is characterized by low volatility and low pack aroma.

It is a further object of this invention to provide novel pyrazine-containing polyheterocyclic compounds adapted for utility as flavorant additives in smoking compositions and foodstuffs.

Other objects and advantages of the present invention shall become apparent from the accompanying description and examples.

DESCRIPTION OF THE INVENTION

One or more objects of the present invention are accomplished by the provision of a polyheterocyclic compound corresponding to the formula:

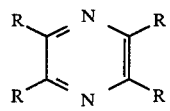

wherein R is a substituent selected from hydrogen and alkyl groups containing between 1 and about 10 carbon atoms; X is a substituent selected from pyrazyl and alkyl-substituted pyrazyl, where each alkyl group contains between 1 and about 10 carbon atoms, and the X substitutent contains a total of between 4 and about 16 carbon atoms; $X^1$ is a substituent selected from pyrazyl, alkyl-substituted pyrazyl, pyridyl and alkyl-substituted pyridyl, where each alkyl group contains between 1 and about 10 carbon atoms, and the $X^1$ substituent contains a total of between 4 and about 22 carbon atoms; and any adjacent R and X or any adjacent R and $X^1$ when taken together with connecting elements form an alicyclic structure.

Illustrative of alkyl groups containing between 1 and about 10 carbon atoms are methyl, ethyl, propyl, isopropyl, butyl isobutyl, pentyl, hexyl, octyl, decyl, and the like. The term "alkyl" is meant to include corresponding unsaturated groups such as ethenyl, butenyl heptenyl, and the like.

One or more further objects of this invention are accomplished by the provision of a novel class of polyheterocyclic compounds corresponding to the formula:

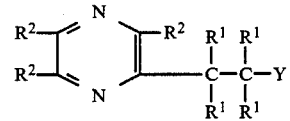

wherein $R^1$ is a substituent selected from hydrogen, methyl and ethyl; $R^2$ is a substituent selected from hydrogen and methyl; and Y is selected from pyrazine and pyridine radicals corresponding to the structures:

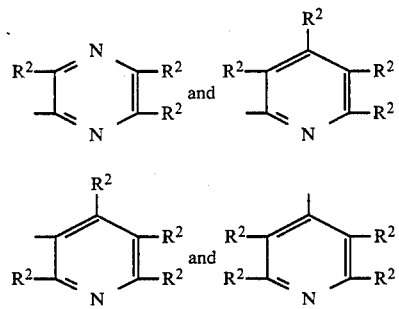

where $R^2$ is as previously defined; and any adjacent $R^1$ and $R^2$ when taken together with connecting elements form an alicyclic structure.

Illustrative of adjacent $R^1$ and $R^2$ taken together with connecting elements to form an alicyclic structure are cyclopentyl, cyclohexyl, cycloheptyl, menthyl, and the like.

A pyrazine-containing polyheterocyclic compound corresponding to the formulae above is a low volatility flavorant which under normal smoking conditions, or other comparable intensively localized heating conditions, volatilizes and evolves as a gasiform component.

A pyrazine-containing polyheterocyclic compound corresponding to the formulae previously described above has a distinct pyrazine odor, quite similar to those of the monomeric pyrazing starting material from which it is derived. However, due to the higher molecular weight, the volatility level of the pyrazine-containing polyheterocyclic compound is greatly reduced in comparison to the corresponding lower molecular weight starting material.

The low level volatility exhibited by a pyrazine-containing polyheterocyclic compound has at least two advantages over a more volatile monomeric pyrazine compound. Firstly, a polyheterocyclic compound has a higher odor threshold which permits it to be utilized as a flavorant additive in a larger quantity; and secondly, the loss of a polyheterocyclic compound (e.g., when employed as a flavorant additive in a smoking composition) due to evaporation and/or sublimation during storage is substantially lessened.

PREPARATION OF POLYHETEROCYCLIC COMPOUNDS

Depending on the structural requirements of a particular compound, the following procedures are illustrative of suitable methods for the synthesis of pyrazine-containing polyheterocyclic compounds of the present invention:

Symmetrical Pyrazines

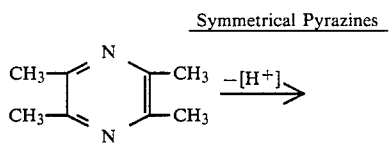

(1)

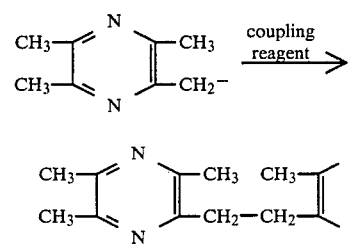

Formation of the anion intermediate is accomplished by treatment of the alkylpyrazine with a strong base such as phenyllithium, lithium diisopropylamide, or alkali metal hydride. Preferably, the base is reacted with the alkylpyrazine starting material in an inert solvent medium maintained at a temperature between about 0° C. and 50° C. under an inert atmosphere. Subsequent treatment of the anion intermediate with a coupling reagent such as oxygen, iodine, bromine, a bromine equivalent such as 1,2-dibromoethylene, or the like, yields the desired dimeric polyheterocyclic compound. With few exceptions, the pyrazine-containing polyheterocyclic compounds of the present invention are odorless, white crystalline solids.

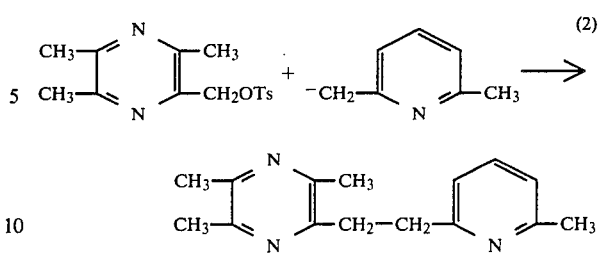

(2)

The monotosylate of pyrazinemethanol is reacted with the anion form of methylpyridine, or conversely, the monotosylate of pyridinemethanol is reacted with the anion form of methylpyrazine.

The same methodology employed for methylpyrazines is applicable to higher homologs. Thus, 2,3,5,6-tetraethylpyrazine is readily coupled to form 2,3-bis(3,5,6-triethyl-2-pyrazyl)butane (as illustrated in Example X).

Procedures for the synthesis of tetraalkylpyrazine starting materials are described in German Offen. 2,140,643 (1973), and the preparation of 2,3-,3,5- and 2,6-dialkylpyrazines is disclosed in U.S. Pat. No. 3,924,015.

Nonsymmetrical Pyrazines

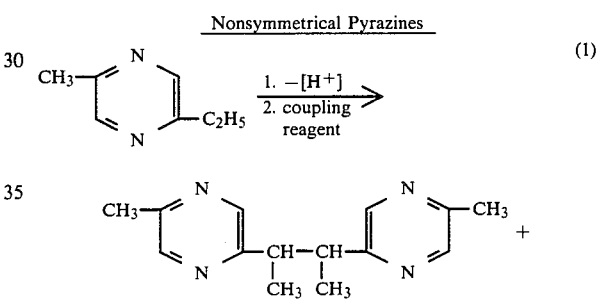

(1)

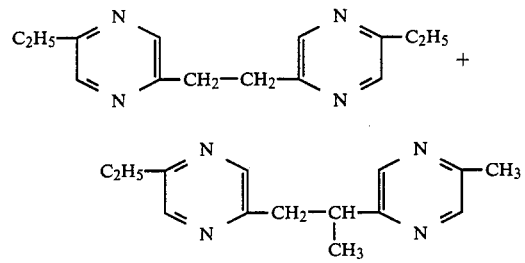

(2)

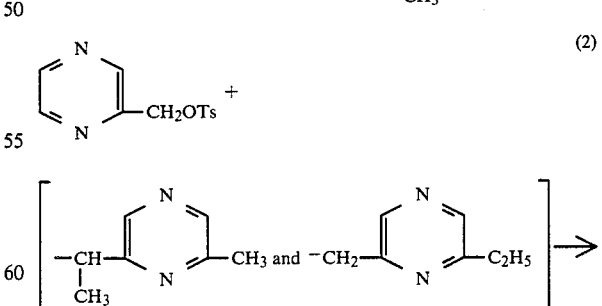

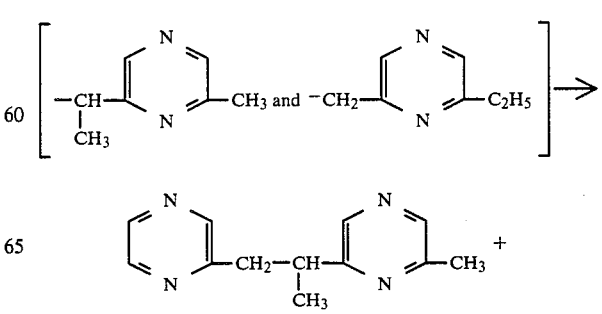

-continued
Nonsymmetrical Pyrazines

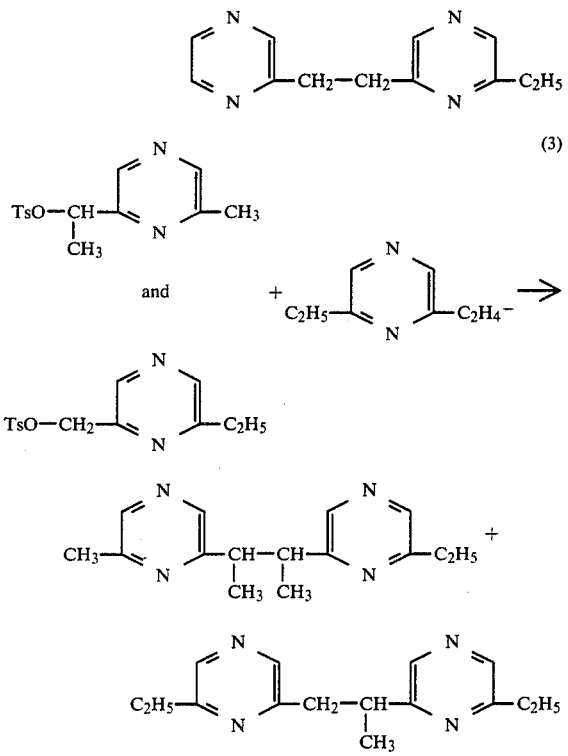

A mixture of polyheterocyclic compounds can be separated by conventional methods such as chromatographic techniques. However, for the purposes of the present invention, a mixture of polyheterocyclic compounds as illustrated hereinabove can be isolated and employed as a flavorant additive per se, without the necessity for fractionating the mixture into separate individual components.

The following examples are further illustrative of the present invention. The reactants and other specific ingredients are presented as being typical, and various modifications can be derived in view of the foregoing disclosure within the scope of the invention.

EXAMPLE I

Preparation Of 1,2-Bis(3,5,6-trimethyl-2-pyrazyl)ethane

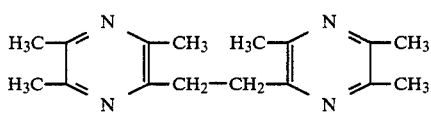

Method A

A solution of 120 grams (1.18 mole) of diisopropylamine in 2 liters of ether was cooled to $-10°$ C., and one liter of a 1.0M n-butyllithium solution in hexane was added. A solution of 136 grams (1.0 mole) of tetramethylpyrazine in 1.5 liters of ether was added while maintaining the temperture of the reaction mixture between $0°$ and $-10°$ C. during addition. After the addition step was completed the reaction mixture was stirred for 10 minutes after which 127 grams (0.5 mole) of iodine in 700 milliliters of ether was added. The reaction mixture was stirred at room temperature overnight, and then it was added to a saturated sodium chloride solution. The organic layer was separated and the aqueous layer was extracted once with ether. The organic portions were combined and dried over sodium sulfate. The solvent was removed and the residue was distilled using a kugelrohr apparatus ($100°$ C. at 0.1 mm mercury). The distillate was recrystallized from hexane to yield 41.75 grams (31%) of a white crystalline solid, m.p. $119°-121.5°$ C.

Method B

To a solution of lithium diisopropylamide (0.05 mole) in 100 milliliters of ether and 20 milliliters of hexane, there was added at $0°$ C., under nitrogen, 6.8 grams (0.05 mole) of tetramethylpyrazine in 40 milliliters of ether. The mixture was stirred at room temperature for 1 hour, after which it was cooled to $9°$ C., and oxygen was passed through it until the red color changed into yellow (about one hour). Water was added, followed by the addition of a large excess of sodium sulfite. The ether layer was separated, and the aqueous layer was extracted once with methylene chloride. The combined organic extracts were dried over magnesium sulfate. Removal of the solvent yielded 6.5 grams of an oil, from which 865 mg (13%) of the desired pyrazine dimer was obtained. Recrystallization of the dimer from hexane gave plates, m.p. $117°-119°$ C. Also isolated was 1.40 grams of 3,5,6-trimethylpyrazine-2-methanol, m.p. $67°-69°$ C., purified by sublimation.

EXAMPLE II

Preparation Of 1,2-Bis(6-methyl-2pyrazyl)ethane

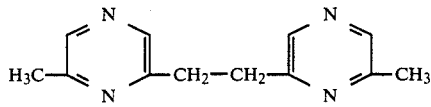

The reaction of 5.40 grams (0.05 mole) of 2,6-dimethylpyrazine with 0.05 mole of lithium diisopropylamide and 6.35 grams (0.025 mole) of iodine was carried out as described in Method A of Example I. A crude product was obtained as previously described and the dimeric pyrazine was purified by elution chromatography to yield 1.9 grams (36%) of pure material. Recrystallization from hexane gave plates, m.p. $99°-101°$ C.

EXAMPLE III

Preparation Of 1,2-Bis(3-methyl-2-pyrazyl)ethane

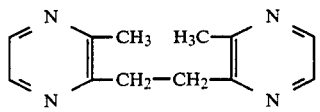

Method A

The reaction of 5.40 gram (0.05 mole) of 2,3-dimethylpyrazine with 0.05 mole of lithium diisopropylamide and 6.35 grams (0.025 mole) of iodine was performed in the manner described in Method A of Example I. A crude product was obtained as before and the dimeric pyrazine was isolated by preparative thin layer chromatography to yield 2.3 grams (43%) of pure material. Recrystallization from hexane gave plates, m.p. $94°-96°$ C.

Method B

To a solution of 0.1 mole of lithium diisopropylamide in 150 milliliters of ether at 0° C., under nitrogen, was added a solution of 10.8 grams (0.1 mole) of 2,3-dimethylpyrazine in 50 milliliters of ether. The mixture was stirred for 20 minutes, and a solution of 18.6 grams (0.1 mole) of 1,2-dibromoethylene in 40 milliliters of ether was added at 0° C. Stirring was continued for 40 minutes, after which period water was added. The ether layer was separated and the aqueous layer was extracted first with ether and then with methylene chloride. The combined organic exerts were dried over magnesium sulfate and the solvent was removed to yield 21 grams of crude product. One gram of the crude mixture was subjected to preparative thin layer chromatography and there was obtained 280 mg (55%) of the dimeric pyrazine. Recrystallization from hexane gave plates, m.p. 94°–96° C.

EXAMPLE IV

Preparation Of 5,5'-Bis(5,6,7,8-tetrahydroquinoxaline)

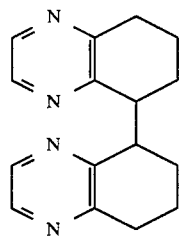

The reaction of 2.68 grams (0.02 mole) of 5,6,7,8-tetrahydroquinoxaline with 0.02 mole lithium diisopropylamide at 0° C. under nitrogen gave the corresponding anion, which was in turn treated with oxygen until the red color disappeared. To the cold solution was added 0.05 mole HCl in 30 milliliters of water. A large excess of sodium sulfite was then added, and the mixture was basified with sodium carbonate to a pH of 9. The ether layer was separated, washed with water, and dried over magnesium sulfate. Evaporation of the solvent yielded 1.1 grams of an oil. The dimeric pyrazine was isolated using preparative thin layer chromatography. The product yield was 260 mg (10%) and consisted of a 4:1 mixture of the meso and d,l-forms. Assignment of stereochemistry could not be done. The material was recrystallized from hexane to give needles, m.p. 110°–114° C. Only the major isomer crystallized.

EXAMPLE V

Preparation Of 1-(3-Methyl-2-pyrazyl)-2-(3,5,6-trimethyl-2-pyrazyl)ethane

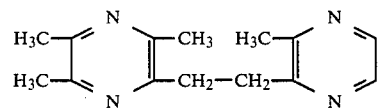

A solution of 0.83 grams (5.5 millimole) of 3,5,6-trimethylpyrazine-2-methanol, obtained by preparative tlc of the reaction mixture obtained by Method B of Example I, in 40 milliliters of ether was added to a 5.5 millimolar solution of lithium diisopropylamide in 50 milliliters of ether. The mixture was stirred for 90 minutes after which period a solution of 1.05 grams (5.5 millimole) of p-toluenesulfonyl chloride in 40 milliliters of ether was added, and the resulting mixture was stirred for an additional 90 minutes. To the solution was added a suspension of 2,3-dimethylpyrazine anion [prepared from 0.594 grams (5.5 millimole) of 2,3-dimethylpyrazine and an equimolar amount of lithium diisopropylamide] in 100 milliliters of ether. Stirring was continued for two hours, after which period water was added and the ether layer was separated. The ether solution was washed with water and dried over magnesium sulfate. Evaporation of the solvent yielded an oil from which 0.65 gram (49%) of the desired product was isolated by preparative thin layer chromatography. An analytical sample, m.p. 42°–44° C., was obtained by sublimation.

EXAMPLE VI

Preparation Of 1-(6-Methyl-2-pyrazyl)-2-(3-methyl-2-pyrazyl)ethane

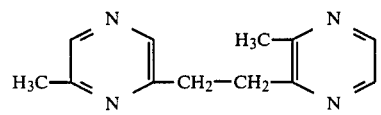

The preparation of 6-methylpyrazine-2-methanol is accomplished by the oxygenation of the corresponding anion. A sample of 1.24 grams (0.01 mole) of 6-methylpyrazine-2-methanol is treated with 0.01 mole of lithium diisopropylamide and 1.91 grams (0.01 mole) of p-toluenesulfonyl chloride as described in Example V. The resulting tosylate is then treated with a suspension of 2,3-dimethylpyrazine anion [prepared from 1.08 grams (0.01 mole) of 2,3-dimethylpyrazine and an equimolar amount of lithium diisopropylamide] in ether. The reaction product is recovered as in Example V, and the dimeric pyrazine is isolated by preparative thin layer chromatography.

EXAMPLE VII

Preparation Of 1-(3,5,6-trimethyl-2-pyrazyl)-2-(2-pyridyl)ethane

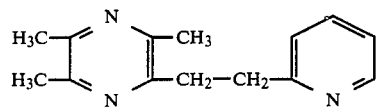

The preparation of 1-(3,5,6-trimethyl-2-pyrazyl)-2-(2-pyridyl)ethane is carried out by the method described in Example V using 1.09 grams (0.01 mole) of pyridine-2-methanol, 1.91 grams (0.01 mole) of p-toluenesulfonyl chloride, and 1.36 grams (0.01 mole) of tetramethylpyrazine. The product is isolated by preparative thin layer chromatography.

EXAMPLE VIII

Preparation Of 1-(6-Methyl-2-pyrazyl)-2-(3-pyridyl)ethane

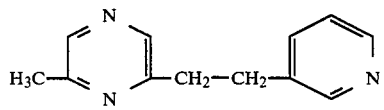

The preparation of 1-(6-methyl-2-pyrazyl)-2-(3-pyridyl)ethane is carried out by the method described in Example V using 1.09 grams (0.01 mole) of pyridine-3-methanol, 1.91 grams (0.01 mole) of p-toluenesulfonyl chloride, and 1.08 grams (0.01 mole) of 2,6-dimethylpyrazine. The product is isolated by preparative thin layer chromatography.

EXAMPLE IX

Preparation Of
1-(3,5,6-Trimethyl-2-pyrazyl)-2-(6-methyl-2-pyridyl)ethane

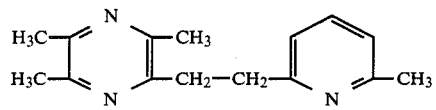

The preparation of 1-(3,5,6-trimethyl-2-pyrazyl)-2-(6-methyl-2-pyridyl)ethane is carried out by the method described in Example V using 1.23 grams (0.01 mole) of 6-methylpyridine-2-methanol, 1.91 grams (0.01 mole) of p-toluenesulfonyl chloride, and 1.36 grams (0.01 mole) of tetramethylpyrazine. The product is isolated by preparative thin layer chromatography.

EXAMPLE X

Preparation Of 2,3-Bis(3,5,6-triethyl-2-pyrazyl)butane

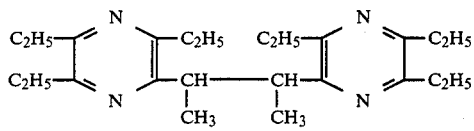

The reaction of 9.60 grams (0.05 mole) of tetraethylpyrazine with 0.05 mole of lithium diisopropylamide and 6.35 grams (0.025 mole) of iodine is carried out as described in Method A of Example I. The crude product is obtained as before, and the dimeric pyrazine is isolated by preparative thin layer chromatography.

EXAMPLE XI

Preparation Of
1-(3,5,6-Trimethyl-2-pyrazyl)-2-(6-methyl-2-pyridyl)propane and
1-(3,5,6-Trimethyl-2-pyrazyl)-2-(6-ethyl-2-pyridyl)ethane

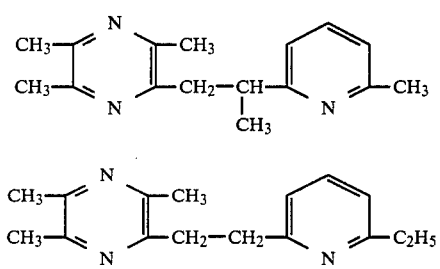

A solution of 3.04 grams (0.02 mole) of 3,5,6-trimethylpyrazine-2-methanol (Method B, Example I) in 150 milliliters of ether is converted to the p-toluenesulfonate as in Example V using 0.02 mole of lithium diisopropylamide in 200 milliliters of ether and 3.82 grams (0.02 mole) of p-toluenesulfonyl chloride in 150 milliliters of ether. The resulting solution is treated with the mixed anion of 2-methyl-6-ethylpyridine [K. S. N. Prasad & R. Raper, J. Chem. Soc., 217 (1956)] formed from the reaction of 2.42 grams (0.02 mole) of 2-methyl-6-ethylpyridine in 80 milliliters of ether and 0.02 mole of lithium diisopropylamide in 200 milliliters of ether. A crude product is obtained as before and the mixture of the two polyheterocyclic compounds is isolated by elution chromatography.

EXAMPLE XII

Preparation Of
1-(6-Propyl-2-pyrazyl)-2-(2-pyridyl)butane and
3-(6-Methyl-2-pyrazyl)-4-(2-pyridyl)hexane

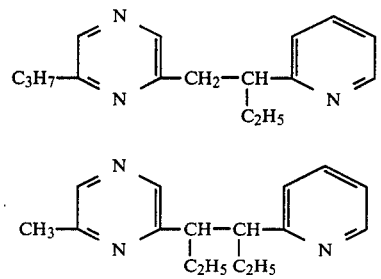

A solution of 4.11 grams of 2-(1-hydroxypropyl)pyridine (0.03 mole), prepared by the addition of ethylmagnesium bromide to pyridine-2-carboxaldehyde, in ether is treated with 0.03 mole lithium diisopropylamide in ether followed by the addition of 5.73 grams (0.03 mole) of p-toluensulfonyl chloride in ether. The solution of the tosylate so formed is treated with a solution of the anion formed by treating 4.08 grams of 2-methyl-6-propylpyrazine [Levine and Behun, J. Org. Chem., 26, 3379 (1961)] with 0.03 mole of lithium diisopropylamide in ether. A crude product is obtained as before and the mixture of the two polyheterocyclic compounds is isolated by elution chromatography.

EXAMPLE XIII

Preparation Of
1-(3,5,6-Trimethyl-2-pyrazyl)-2-(6-butyl-2-pyrazyl)ethane and
1-(3,5,6-Trimethyl-2-pyrazyl)-2-(6-methyl-2-pyrazyl)pentane

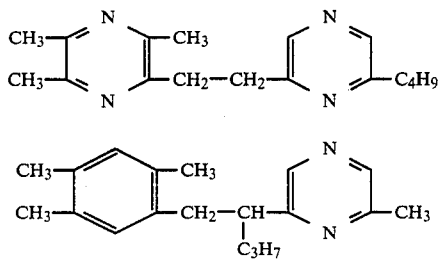

A solution of 3.04 grams (0.02 mole) of 3,5,6-trimethylpyrazine-2-methanol (Method B, Example I) in 150 milliliters of ether is converted to the p-toluenesulfonate as in Example V using 0.02 mole of lithium diisopropylamide and 3.82 grams (0.02 mole) of p-toluenesulfonyl chloride. The resulting solution is treated with the mixed anion of 2-butyl-6-methylpyrazine, prepared by the method of Levine and Behun, using 3.00 grams (0.02 mole) of the pyrazine and 0.02 mole of lithium diisopropylamide. The mixture of the two polyheterocyclic compounds is isolated by elution chromatography.

EXAMPLE XIV

Preparation And Testing Of Flavored Tobacco Compositions

A solution of 1,2-bis(3,5,6-trimethyl-2-pyrazyl)ethane in ethanol was injected into a cigarette (designed to deliver 8 mg FTC tar) to provide a final application level of 1000 ppm of the polyheterocyclic flavorant. Cigarettes were smoked by a panel of four experts and compared to the identical cigarette without added flavorant. Three out of four panelists found the treated cigarette to be considerably smoother.

A solution of 1,2-bis(6-methyl-2-pyrazyl)ethane in ethanol was injected into a cigarette (designed to deliver 8 mg FTC tar) to provide a final application level of 200 ppm of the polyheterocyclic flavorant. Cigarettes were smoked by a panel of four experts and compared to the identical cigarette without added flavorant. All four panelists found the treated cigarette to be considerably smoother.

What is claimed is:
1. 1,2-Bis(3,5,6-trimethyl-2-pyrazyl)ethane.
2. 1,2-Bis(6-methyl-2-pyrazyl)ethane.
3. 1,2-Bis(3-methyl-2-pyrazyl)ethane.
4. 1-(3-Methyl-2-pyrazyl)-2-(3,5,6-trimethyl-2-pyrazyl)ethane.
5. 1-(6-Methyl-2-pyrazyl)-2-(3-methyl-2-pyrazyl)ethane.
6. 1-(3,5,6-Trimethyl-2-pyrazyl)-2-(2-pyridyl)ethane.
7. 1-(6-Methyl-2-pyrazyl)-2-(3-pyridyl)ethane.
8. 1-(3,5,6-Trimethyl-2-pyrazyl)-2-(6-methyl-2-pyridyl)ethane.
9. A process for preparing a polyheterocyclic compound which comprises the steps of (1) dissolving and interacting in a solvent medium a basic reagent and an organic compound corresponding to the formula:

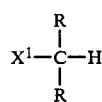

where R is a substituent selected from hydrogen and alkyl groups containing between 1 and about 10 carbon atoms; $X^1$ is a substituent selected from pyrazyl, alkyl-substituted pyrazyl, pyridyl and alkyl-substituted pyridyl, where each alkyl group contains between 1 and about 10 carbon atoms, and the $X^1$ substituent contains a total of between 4 and about 22 carbon atoms; and any adjacent R and X or any adjacent R and $X^1$ when taken together with connecting elements form an alicyclic structure; wherein the interaction converts the organic compound into an anion corresponding to the structure:

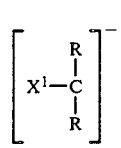

where R and $X^1$ are as previously defined; and (2) treating the solvent medium containing the anion with a coupling reagent to cause dimeric coupling of the anion to form a polyheterocyclic compound corresponding to the formula:

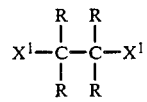

where R and $X^1$ are as previously defined.

10. A process for preparing a polyheterocyclic compound which comprises dissolving and interacting in a solvent medium (a) a basic reagent, (b) at least one sulfonate ester compound corresponding to the formula:

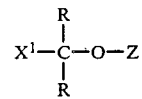

where R is a substituent selected from hydrogen and alkyl groups containing between 1 and about 10 carbon atoms; $X^1$ is a substituent selected from pyrazyl, alkyl-substituted pyrazyl, pyridyl and alkyl-substituted pyridyl, where each alkyl group contains between 1 and about 10 carbon atoms, and the $X^1$ substituent contains a total of between 4 and about 22 carbon atoms; and any adjacent R and X or any adjacent R and $X^1$ when taken together with connecting elements form an alicyclic structure; and Z is an organosulfonyl radical, and (c) at least one compound corresponding to the formula:

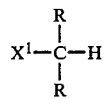

where R and $X^1$ are as previously defined; wherein the interaction yields a polyheterocyclic compound corresponding to the formula:

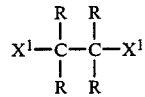

where R and $X^1$ are as previously defined.

* * * * *